United States Patent [19]

Levine et al.

[11] 4,096,824
[45] Jun. 27, 1978

[54] SLIDE SMEARING DEVICE

[75] Inventors: Marshall S. Levine, Wayne; Albert A. Faulkner, Conshohocken, both of Pa.

[73] Assignee: SmithKline Corporation, Philadelphia, Pa.

[21] Appl. No.: 703,939

[22] Filed: Jul. 9, 1976

[51] Int. Cl.² .......................................... B05C 11/04
[52] U.S. Cl. ................................... 118/100; 118/120; 118/236; 118/506; 8/3; 424/3; 427/2
[58] Field of Search .............. 118/100, 104, 120, 236, 118/237, 506, 7; 427/2, 4; 424/3; 8/3; 204/180 S, 180 G; 23/230 B

[56] References Cited

U.S. PATENT DOCUMENTS

| 1,858,308 | 5/1932 | Schiller | 118/100 |
| 3,175,646 | 3/1965 | Wilcox | 188/94 |
| 3,467,060 | 9/1969 | Klebanow et al. | 118/236 |
| 3,589,557 | 6/1971 | Johnson | 118/100 X |
| 3,683,850 | 8/1972 | Grabhorn | 118/100 |
| 3,871,895 | 3/1975 | Adler | 427/2 |
| 3,880,111 | 4/1975 | Levine et al. | 118/100 X |
| 3,985,096 | 10/1976 | Guimbretiere | 118/236 X |
| 4,034,700 | 7/1977 | Bassett et al. | 118/100 X |

FOREIGN PATENT DOCUMENTS

| 439,124 | 1/1927 | Germany | 118/100 |
| 1,166,088 | 10/1969 | United Kingdom | 118/236 |

Primary Examiner—James Kee Chi
Attorney, Agent, or Firm—Smith, Harding, Earley & Follmer

[57] ABSTRACT

A device for smearing on slides a drop of liquid placed on a predetermined point on each slide has slide magazines containing a plurality of slides with the uppermost slide in each magazine having its upper face exposed for the reception of a drop of liquid towards one end thereof. Spreaders are adjacent the other ends of the slides. Means advance the spreaders out of contact with the slides, lower the spreaders into contact with the slides as they approach said predetermined points on the slides and slow the advance of the spreaders as they approach said points. The spreaders are retracted and the angle between each spreader and slide decreases to thin the smear of liquid. Means advance the uppermost slide in each magazine forwardly out of the magazine a predetermined distance to facilitate the removal of the slide by hand after the desired smear is made.

21 Claims, 19 Drawing Figures

SLIDE SMEARING DEVICE

BACKGROUND OF THE INVENTION

It is well known to smear a liquid on a slide and then subject the liquid to examination under a microscope. This is done widely, for example, with blood to make a white blood cell differential count. The quality of the smear is important, for example, automatic blood cell differential analyzers cannot provide an accurate white blood cell differential count unless there is an adequate uniform area of blood cell monolayer in the smear. Not only is it important to provide a good smear, but it is also important to provide a uniformity of smear from one slide to another.

Prior art devices for smearing a slide are shown in the following patents: German Pat. No. 439,124, Jan. 24, 1927; U.S. Pat. No. 3,683,850, Aug. 15, 1972; and U.S. Pat. No. 3,880,111, Apr. 29, 1975. The device of the German patent is markedly different structurally and is unsatisfactory since it is not possible manually to control the speed of the spreader while smearing to provide either a good smear or smears which are uniform from one smear to the other. While U.S. Pat. Nos. 3,683,850 and 3,880,111 disclose satisfactory devices they are markedly different structurally and lack the highly advantageous features provided by the invention. While slide magazines are known the prior art fails to teach the employment of a slide magazine which permits smearing a liquid on a slide in the magazine. The magazine eliminates unwanted touching of the slides and provides for the easy removal of a slide after it is smeared. Spreader wear is markedly reduced by keeping the spreader out of contact with the slide until it approaches the point on the slide where it is to contact the liquid. The device of the invention has novel means to slow the advance of the spreader as it approaches the position on the slide where the liquid is to be contacted. While manually actuated, the invention provides automatic timing of the dwell time for the spreading of the liquid on the spreaders. Novel means are provided for varying the angles of the spreaders to provide a wedge smear.

BRIEF SUMMARY OF THE INVENTION

A device for smearing on a slide a drop of liquid placed on a predetermined point on the slide has a slide magazine containing a plurality of slides with the uppermost slide having its upper face exposed for the reception of a drop of liquid towards one end thereof. A spreader is adjacent the other end of the slide. Means advance the spreader to said predetermined point on the slide and retract the spreader to its original position. Advantageously, the invention has means to advance the uppermost slide laterally out of the magazine a predetermined distance to facilitate the removal of the slide by hand. The invention also involves a number of additional aspects which may be employed with or without the magazine. Advantageously, the spreader advancing and retracting means maintains the spreader out of contact with the slide as it advances until it approaches said predetermined point on the slide when the spreader is lowered into contact with the slide. The spreader advancing and retracting means may include cam means to reduce the speed of advance of the carrier as it approaches said predetermined point on the slide. The invention also advantageously has means to decrease and then increase the angle between the spreader and the slide as the spreader is retracted to control the thickness of the smear of liquid. When a magazine is employed, it is preferred to have an indicator on the magazine to indicate where the liquid should be placed on the slide. The invention is manually actuated and has means to automatically provide a dwell time for the liquid to spread along the spreader. Preferably multiple magazines and spreaders are employed. Air means may be employed to assist in drying the smeared liquid. A magazine for use with the spreader device has an open top for the spreading of a liquid on the uppermost slide, means to permit the removal of two slides stuck together and means to temporarily retain the slides in the magazine. Permanent means to hold the slides in the magazine are also provided as are means to retain the slides separated in the magazine to prevent them from sticking together.

DETAILED DESCRIPTION

Figure 1:
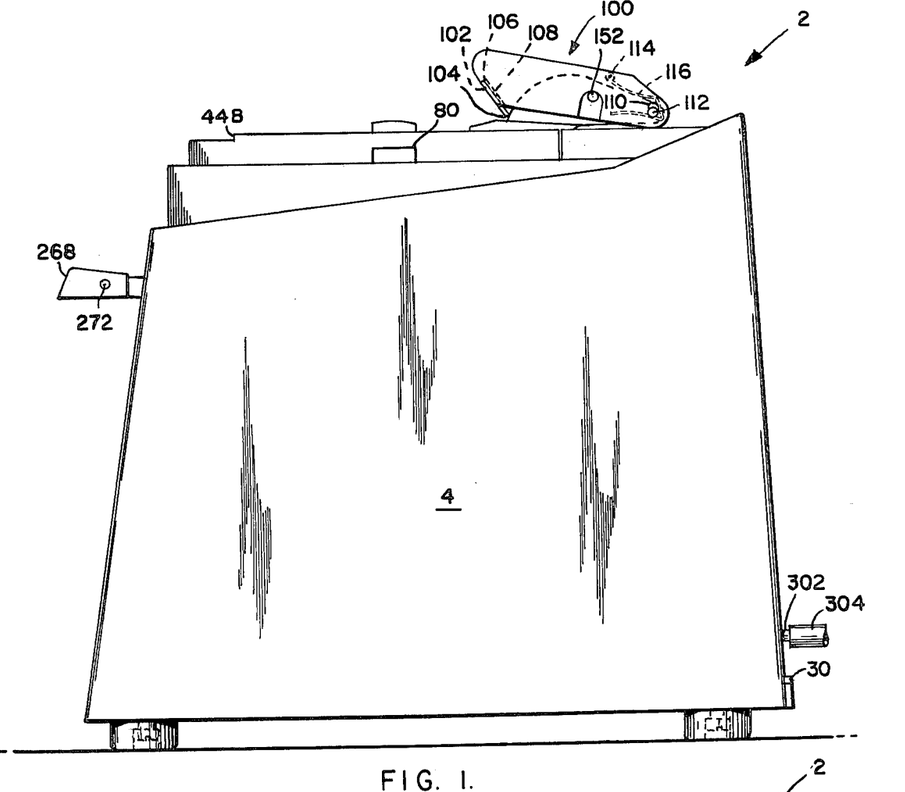
FIG. 1 is a right side elevation of a slide smearing device in accordance with the invention.
Figure 2:
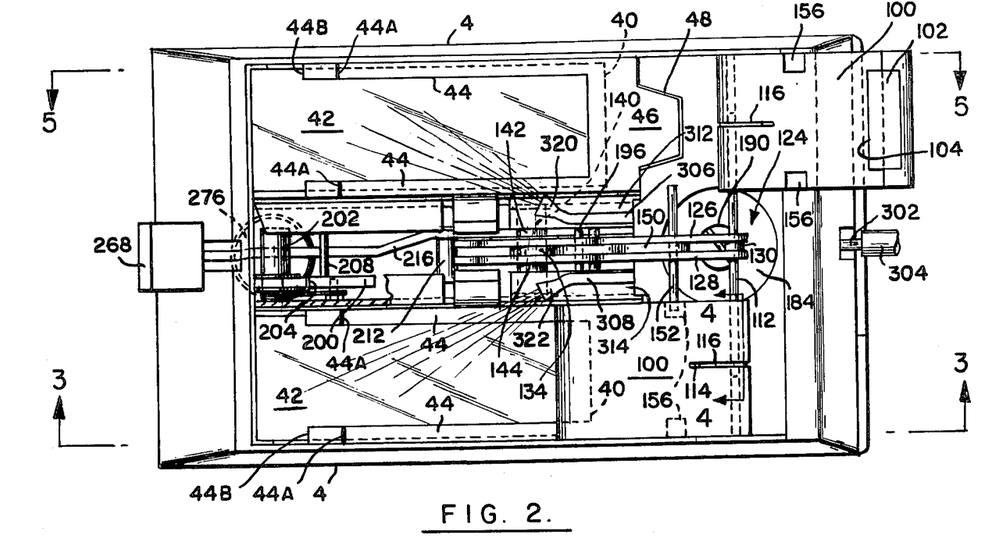
FIG. 2 is a top plan view of the device of FIG. 1.
Figure 3:
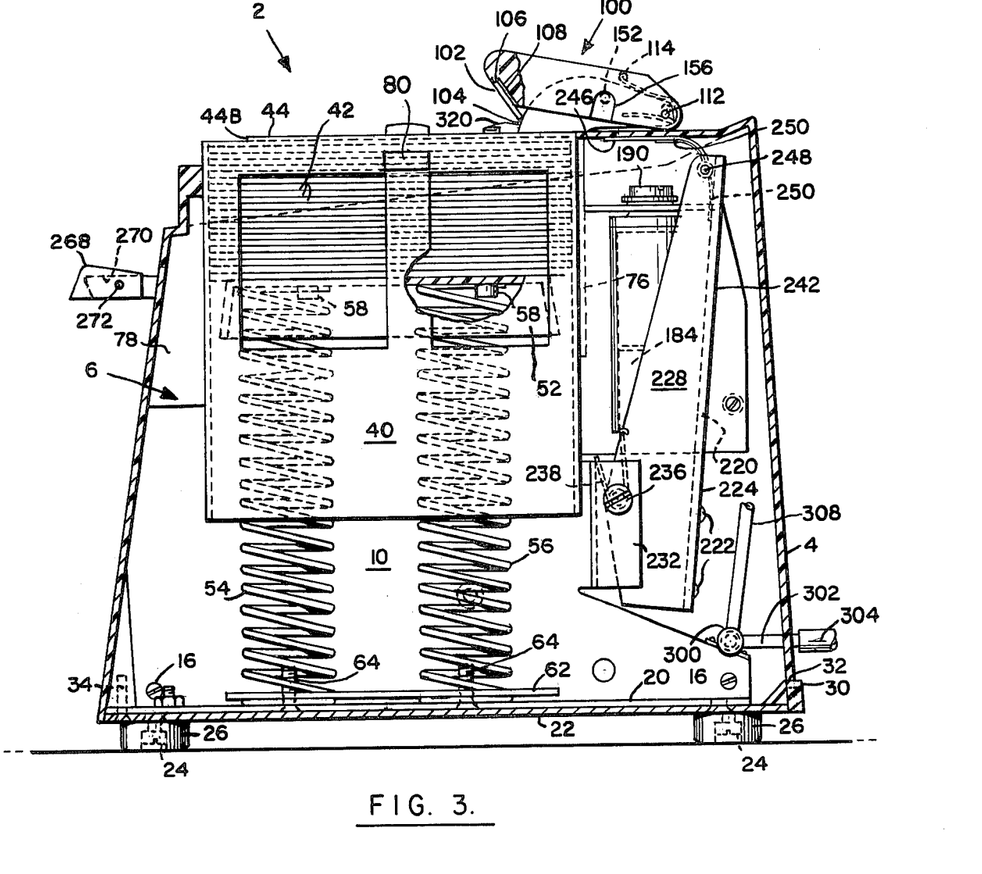
FIG. 3 is a vertical section taken on the plane indicated by the line 3—3 in FIG. 2.

A slide smearing device 2 in accordance with the invention has a removable casing 4 (FIGS. 1 and 2). A frame 6 (FIG. 9) within casing 4 has a pair of upstanding plates 8 and 10 which are retained in spaced relation by a plurality of rods 14 secured to plates 8 and 10 respectively by screws 16, 16. Plates 8 and 10 respectively have supporting flanges 18 and 20 which rest on a bottom plate 22. Screws 24 hold rubber feet 26 to plate 22. As best seen in FIG. 3 bottom plate 22 has a tongue 30 which passes through a slot 32 in casing 4 to support one end of the bottom plate and the other end of the bottom plate is secured to casing 4 by means of screws 34.

Figure 8:
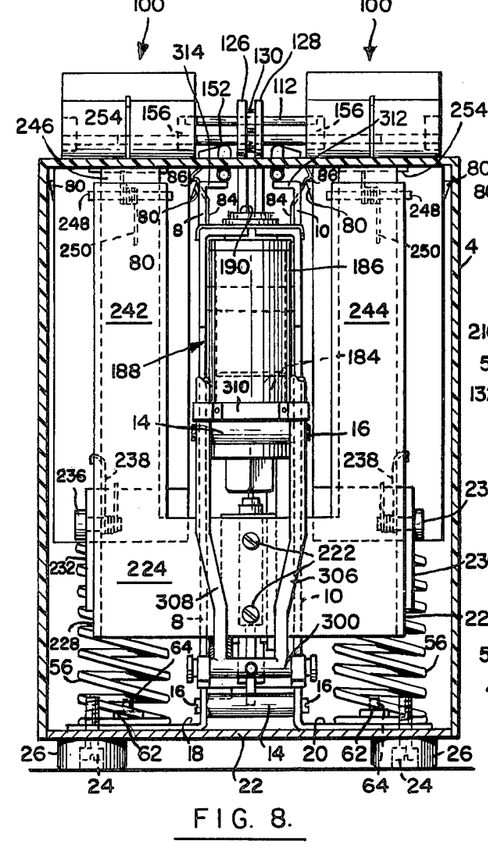
FIG. 8 is a vertical section taken on the plane indicated by the line 8—8 in FIG. 5.

Adjacent each plate 8 and 10 of frame 6 is a slide magazine 40 (FIG. 9) containing a stack of glass microscope slides 42. Each magazine 40 at its upper end has a U-shaped flange 44 (FIG. 2) to retain the uppermost slide 42 while permitting it to be pulled out from the front end of the magazine. The upper end of each magazine 40 also has a tongue 46 which fits into an opening 48 in the top of casing 4. The magazine is supported by virtue of a cap member 52 (FIG. 3) inside the magazine the upper end of which bears against the lowest of the slides 42. A pair of compression coil springs 54 and 56 have their upper ends secured to the interior of cap 52 as indicated at 58 and each has its lowermost coil held down to flange 18 or 20 of frame 6 as appropriate by a bar 62 which is secured to the flange by screws indicated at 64. Casing 4 has vertical guide members indicated at 76 and 78 to assist in holding each magazine 40 in the desired position. Each magazine 40 has a pair of opposed bosses 80, 80 with one of the bosses adjacent a leaf spring 84 having a clip portion 86 which engages boss 80. (See FIGS. 8 and 9). A leaf spring 84 is secured to each of walls 8 and 10 by screws 88.

Mounted above each slide 42 is a spreader 100. Each spreader 100 has a rectangular glass panel 102 (FIG. 3) having a lower edge 104 adapted to engage a slide. Panel 102 is received in a recess 106 in which it is retained by a strip of double adhesive tape 108. Each spreader 100 has a slot 110 which receives a pin 112 with sufficient vertical clearance between the spreader and the pin to permit the spreader to rock from side to side while restricting side to side movement in a generally horizontal plane. Spreader 100 has a slot 114 at its rear end which receives a spring clip 116 which in turn is received in a groove 118 in pin 112 (FIG. 4) to keep spreader 100 from moving along pin 112 in the direction of the axis of the pin.

Figure 9:
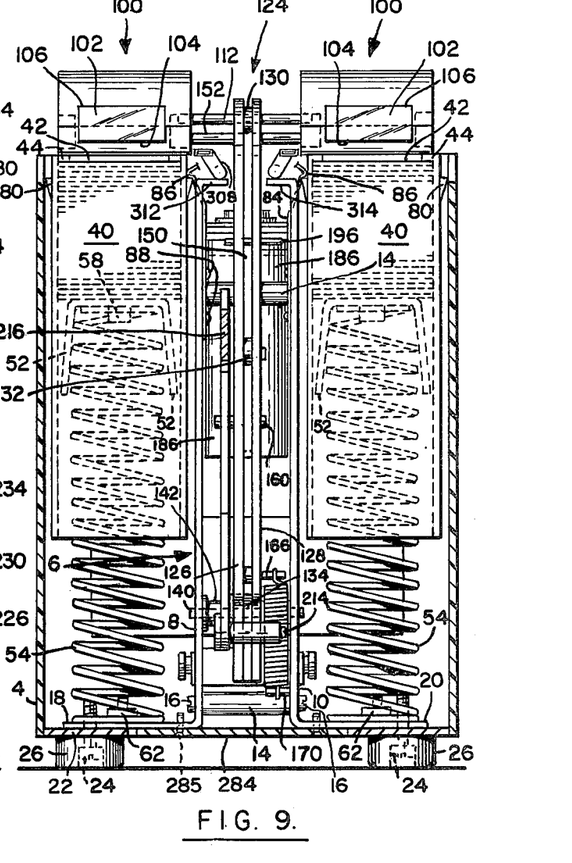
FIG. 9 is a vertical section taken on the plane indicated by the line 9—9 in FIG. 5.

Pin 112 is fixedly secured to a lever 124 (FIG. 2) formed of two arms 126 and 128 which are mirror images of each other and which are spaced apart a fixed distance by spacers 130, 132 and 134 (FIG. 9). Pin 112 passes through spacer 130. Arms 126 and 128 are pivotally mounted on a pin 140 secured by a pressed fit in walls 8 and 10 of frame 6. Pin 140 passes freely through spacer 134 and freely through spacers 142 and 144 which act to space arms 126 and 128 away from walls 8 and 10 respectively (FIG. 2).

An arm 150 (FIG. 5) is mounted for movement between arms 126 and 128 and has fixedly secured to its upper end a pin 152 which extends through a generally vertical slot 154 in arm 126 and a mirror image slot (not shown) in arm 128. Each spreader 100 has opposed slots 156 (FIG. 2) one of which is adapted to engage pin 152 to limit the downward travel of spreader 100. The slots 156 are substantially wider than the diameter of pin 152. A pin 160 fixedly secured to arm 150 (FIG. 5) adjacent its lower end is engaged in a slot 162 having a generally horizontal upward portion 164 as viewed in FIG. 5 in arm 126 and in a mirror image slot (not shown) in arm 128. A pin 166 is secured to arm 128 and in turn is secured to one end of an extension coil spring 168 which has its other end secured to a pin 170 secured to wall 10.

Figure 5:
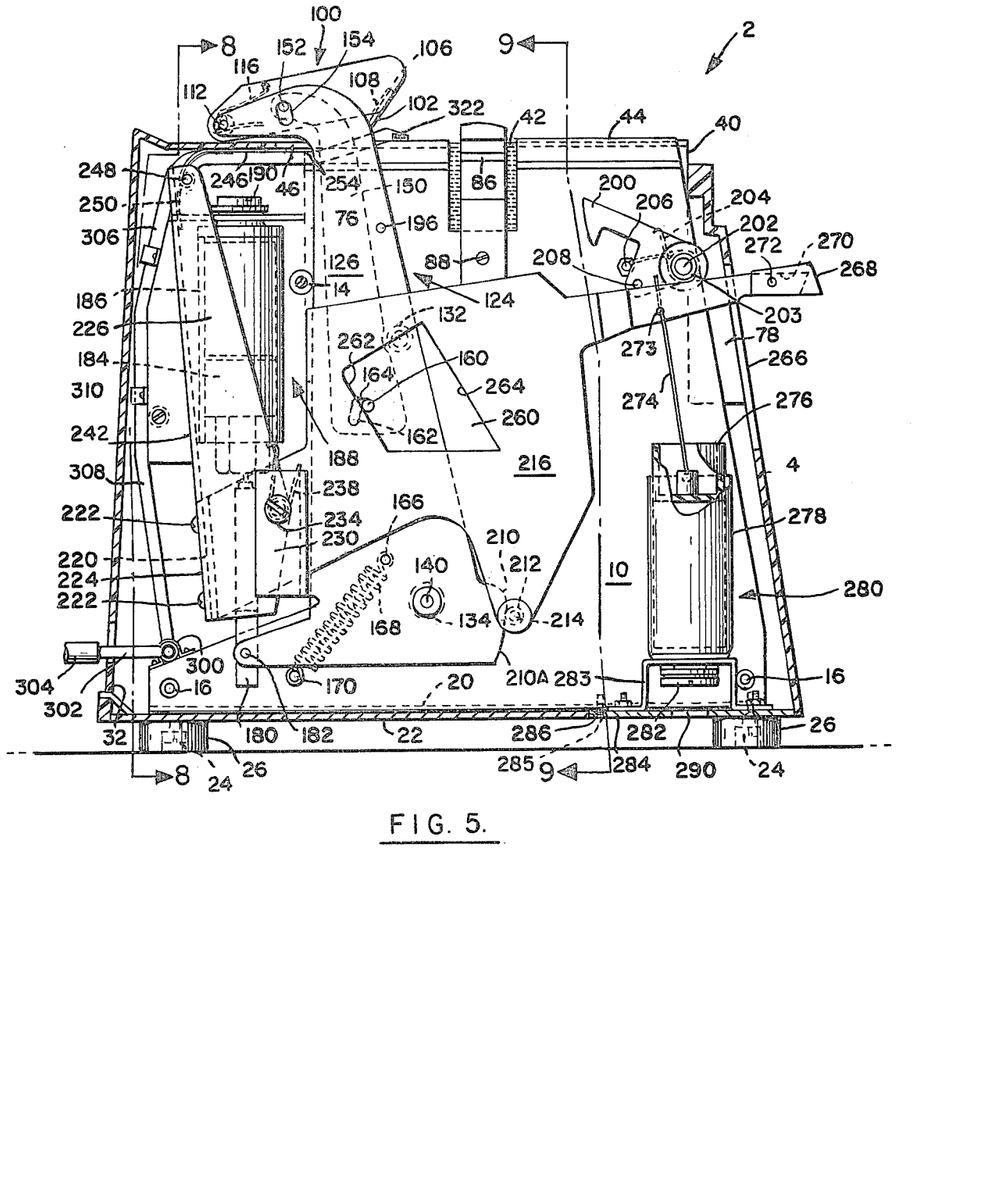
FIG. 5 is a vertical section, partially broken away, taken on the plane indicated by the line 5—5 in FIG. 2.

Spring 168 acts to bias lever 124 to its retracted position shown in FIG. 5.

A rod 180 (FIG. 5) is pivotally mounted between arms 126 and 128 by a pin 182 and has its upper end secured to a plunger 184 in a cylinder 186 of a dashpot 188 having an adjustable valve 190. Dashpot 188 is of the construction shown in FIGS. 1, 2 and 4 of L. C. Wilcox Pat. No. 3,175,646 and hence need not be described in detail here. Dashpot 188 retards lever 124 when it moves counterclockwise as viewed in FIG. 5 preferably providing a selected total smear time in the range of from about 1/5 to about 2 seconds.

Lever 124 has a pin 196 which is fixedly secured to arms 126 and 128 and is adapted to be engaged by a latch 200 which is pivotally mounted on a pin 202 secured to walls 8 and 10, latch 200 being biased in a counterclockwise direction as viewed in FIG. 5 by a torsion spring indicated at 204. The counterclockwise rotation of latch 200 is limited by a screw 206 secured to wall 10. Latch 200 has an actuating pin 208.

Each of arms 126 and 128 has a cam surface 210 engaged by a sleeve 212 of a low friction material, for example, nylon, polyethylene or polypropylene mounted on a pin 214 fixedly secured to the lower end of a lever 216 (FIG. 5). Lever 216 has a flange 220 (FIG. 5) secured by screws indicated at 222 to a U-shaped member 224 which has side flanges 226 and 228 (FIG. 8) respectively pivotally secured to flanges 230 and 232 by pins 234 and 236, flanges 230 and 232 being integral with walls 8 and 10 respectively. Each of pins 234 and 236 supports a torsion spring 238 which acts to bias U-shaped member 224 and lever 216 counterclockwise as viewed in FIG. 5.

Figure 10:
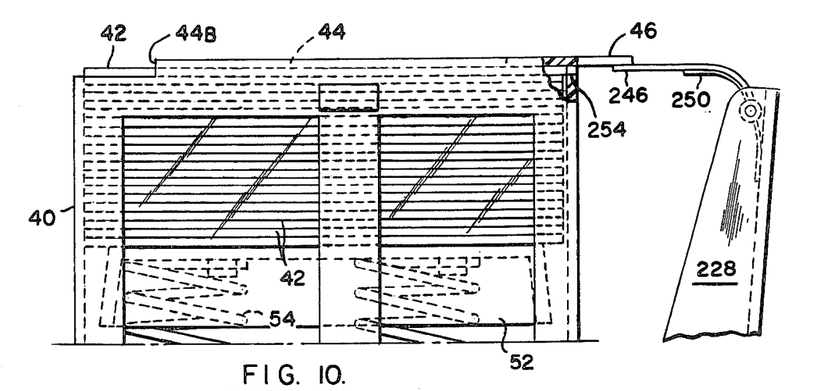
FIG. 10 is an enlarged side elevation, partially broken away, of a magazine of the device of FIG. 1 and an associated pusher in the at rest position.
Figure 11:
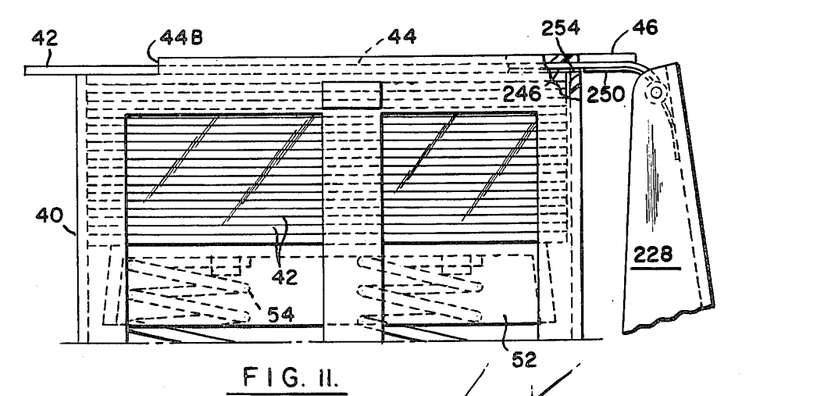
FIG. 11 is a side elevation, partially broken away, of the structure of FIG. 10 showing the pusher in the advanced position.

U-shaped member 224 has a pair of upstanding arms 242 and 244 each of which has a pusher strip 246 of spring steel pivotally mounted at its rear end on a pin 248 and biased upwardly by a torsion spring 250 mounted on pin 248. As best seen in FIGS. 10 and 11 each pusher strip 246 lies below the top of housing 4 and is adapted to lie below the respective magazine tongue 46 and pass into a magazine 40 through a slot 254 below tongue 46 to engage the rear end of the uppermost slide 42. Slot 254 is wide enough to accommodate pusher strip 246 but too narrow to permit a slide 42 to pass through it.

Lever 216 has a cam opening 260 (FIG. 5) which is adapted to receive pin 160 secured to arm 150, opening 260 being bounded by a rear wall 262 which is adapted to cam pin 160 to its uppermost position in slot 162 and a front wall 264 which is adapted to cam pin 160 to its lowermost position in slot 162.

Lever 216 passes through a slot 266 in housing 4 and has a removable finger piece 268 which has a slot 270 for the reception of lever 216 and is secured to the lever by means of a pin indicated at 272. Lever 216 has an opening 273 for the reception of a rod 274 to pivotally connect the rod to lever 216. Rod 274 is pivotally connected to a plunger 276 in a cylinder 278 of a dashpot 280 which has an adjustable valve indicated at 282. Dashpot 280 is of the structure shown in FIGS. 1, 2 and 4 of U.S. Pat. No. 3,175,646 to Wilcox and hence its structure need not be detailed here. Dashpot 280 is mounted on a bracket 283 which in turn is secured to a plate 284 secured to flanges 18 and 20 of frame 6 by screws 285 (FIG. 9) and is received in an opening 286 in bottom plate 22. Plate 284 has an opening 290 to permit the entry of a screwdriver for the adjustment of valve 282. Dashpot 280 retards lever 216 as it moves counterclockwise as viewed in FIG. 5.

A manifold 300 has an inlet pipe 302 connected to an air supply hose 304 supplied with air under pressure from a source not shown and has a pair of upwardly extending discharge lines 306 and 308 (FIG. 8) which are retained by a bracket indicated at 310 and pass upwardly onto flanges 312 and 314 respectively on walls 8 and 10 respectively. The discharge end 320 of line 306 is flattened and directed to the adjacent slide 42 to pass air over the slide. Similarly the discharge end 322 of line 308 is flattened and directed towards the adjacent slide 42 to pass air thereover.

Operation

Figure 6:
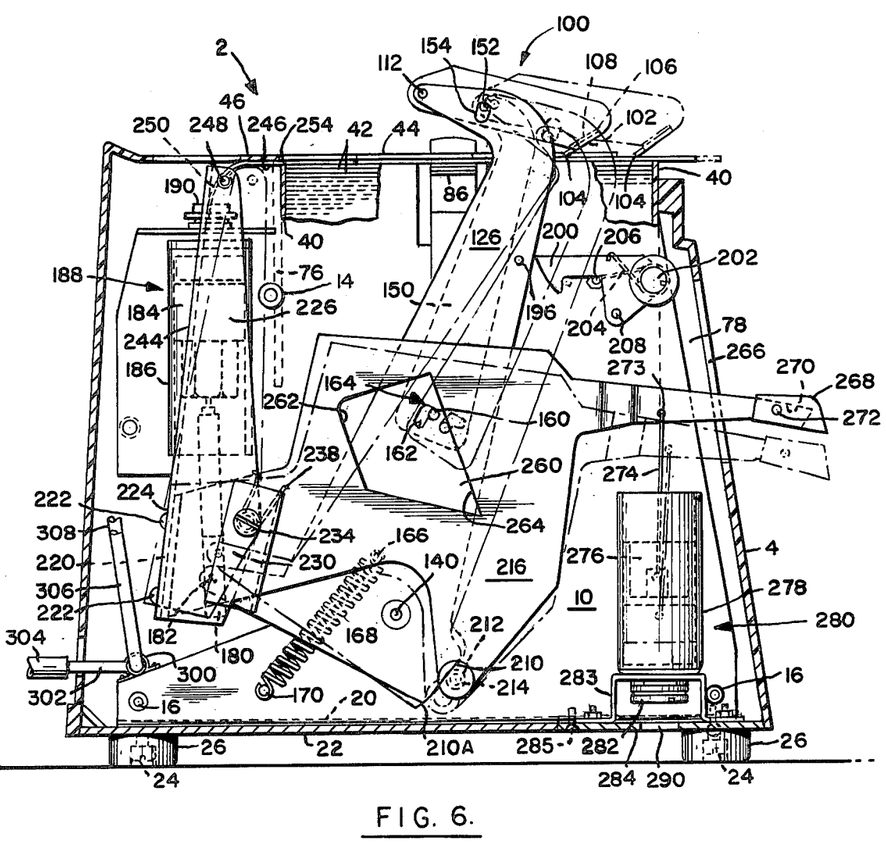
FIG. 6 is the same vertical section as shown in FIG. 5 with the parts being shown in advanced positions.

With the device in the retracted position as shown in FIGS. 1 through 5, a drop of the liquid to be spread is placed on each of the uppermost slides 42 opposite marks 44A on flanges 44. The finger piece 268 is depressed causing lever 216 and U-shaped member 224 to rotate clockwise about pins 234 and 236 as viewed in FIG. 5 which results in advancing pusher strips 246 into magazines 40 to advance slides 42 in each magazine forwardly (FIG. 11). Simultaneously sleeve 212 bears against cam surfaces 210 on lever 124 causing lever 124 to move clockwise about pin 140 as viewed in FIG. 5. As lever 124 is rotated, arm 150 remains in its elevated position with pin 152 being in the upper part of slots 154 and pin 160 being in the upper part 164 of slots 162 maintaining glass panels 102 of spreaders 100 above their respective slides 42 as the spreaders 100 are advanced to avoid wearing the glass panel. As best seen in FIG. 6 the rotation of lever 124 causes glass panels 102 to be lowered so that edges 104 contact slides 42 as they approach the point where the liquid has been deposited thereon. Since the spreaders can rock from side to side on pin 112, the glass panels 102 align themselves with the slides 42 without swinging from left to right. As lever 216 continues to rotate lever 124, the spreaders 100 pivot on pin 112 so as not to impede the rotation of lever 124 and the glass panels 102 are overtaking the liquid on the slides. Shortly after glass panels 102 contact the slides 42 pin 160 on arm 150 is brought against wall 264 on lever 216 forcing pin 160 out of the upper portion 164 of slots 162 causing pin 160 to drop to the lower portion of slot 162 and pin 152 to drop into the lower portion of slots 154 in order than pin 152 be prevented from elevating spreaders 100 prematurely on retraction of the spreaders. The further rotation of lever 124 causes pin 196 to cam latch 200 upwardly permitting the latch 200 to ride over pin 196 and then to be moved downwardly by spring 204 in a position to hold pin 196. The rotation of lever 216 is then arrested by lever 216 contacting the bottom of slot 266. This stops pushers 246 stopping the further advance of the slides 42.

To prevent damage to the liquid, for example, to blood cells when blood is being smeared, cam 210 is cut to gradually reduce the speed of rotation of lever 124 as panels 102 approach the liquid with the portion 210A of cam 210 (FIGS. 5 and 6) reached by sleeve 212 just as the panels 102 reach the liquid lying on an arc with its center on the pivot point of lever 216 at that point so that the speed of rotation of lever 124 has dropped all the way to zero.

Figure 4:
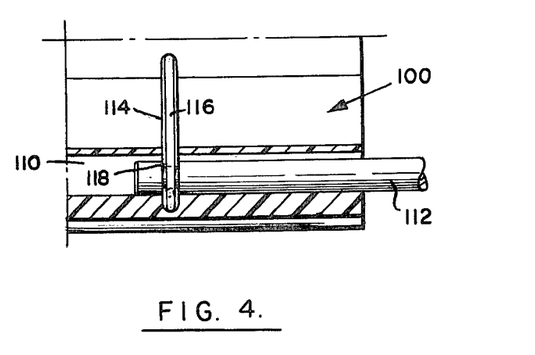
FIG. 4 is a vertical section, partially broken away, taken on the plane indicated by the line 4—4 in FIG. 2.

Handle portion 268 of lever 216 is now released permitting springs 238 to rotate U-shaped member 224 and lever 216 counterclockwise about pins 234 and 236 as viewed in FIG. 4 with the rotation being retarded by dashpot 280 to provide about 2 seconds for the spread of the liquid along glass panels 102. As lever 216 rotates it engages pin 208 on latch 200 causing it to rotate clockwise as viewed in FIG. 5 and release pin 196. The counterclockwise movement of lever 216 is arrested by a rubber sleeve 203 on pin 202. At this juncture, pushers 246 will be fully retracted permitting the next slides 42 in the magazine 40 to move upwardly into position for the next operation when the top slides are removed.

Figure 7:
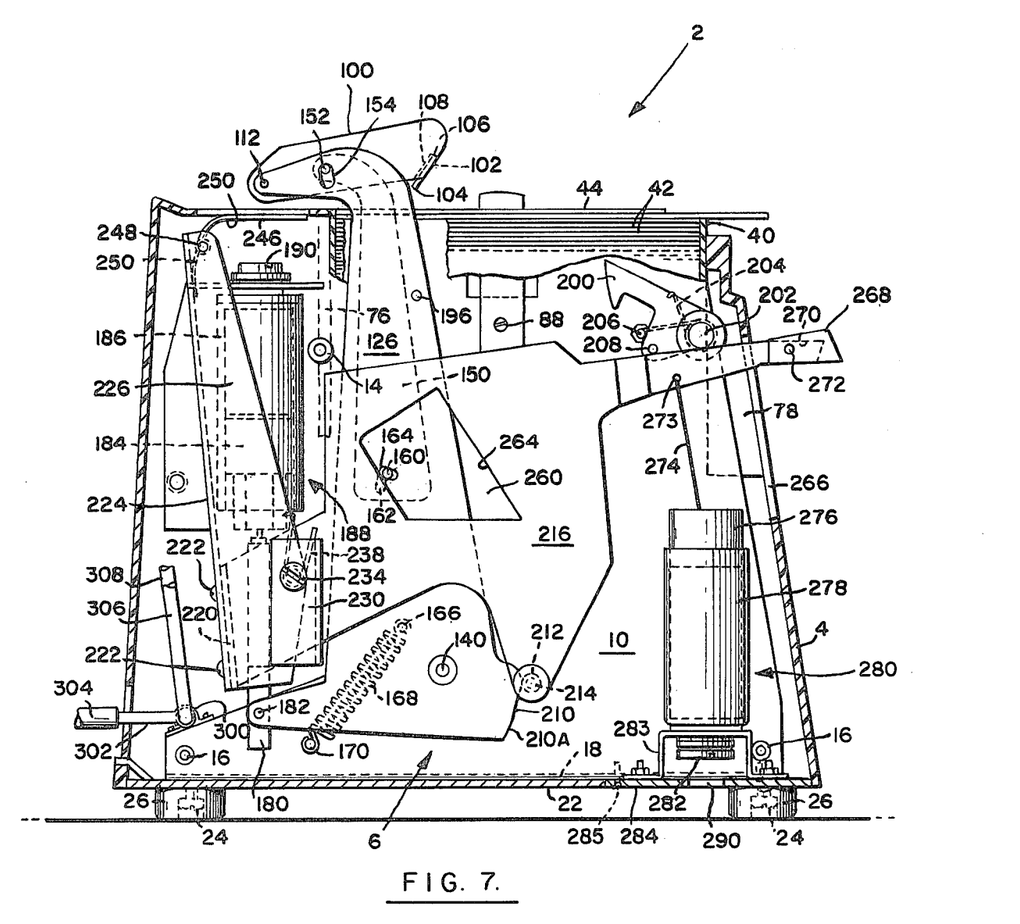
FIG. 7 is the same vertical section shown in FIG. 4 with the parts being shown close to the fully retracted position.

The release of pin 196 from latch 200 causes spring 168 to effect the rotation of lever 124 at a substantially constant speed due to the action of dashpot 188 causing spreaders 100 including glass plates 102 to be retracted along slides 42 and spread the liquid deposited on the slides along the slides. Valve 190 of dashpot 188 permits changing the speed of rotation of lever 124. For example, if thick blood is to be smeared a faster speed will be used than in the case of thin blood. Typically for a 2 inch smear the time will range from 1/5 second to 2 seconds depending on the thickness of the liquid. As retraction proceeds the counterclockwise movement of lever 124 as viewed in FIG. 6 causes the raising of pin 112 which in turn causes a decrease in the angle between the glass plates 102 and the slides 42 resulting in a thinning of the liquid on the slides to promote a wedge shaped smear. Typically, this angle at the commencement of spreading will be sufficiently large to prevent carrying away an excessive amount of liquid, for example, from about 20° to about 50° and desirably will decrease from about 20% to about 50% during the initial spreading. Advantageously the angle at the commencement of spreading is from about 25° to about 35°. Typically the device is designed to have an angle of 28° at the commencement of spreading and the angle will gradually decrease to 20° after which it gradually increases, for example to about 35°, to insure the spreading of any remaining small amount of liquid. As best seen in FIG. 7, as spreaders 100 approach the end of their retraction with the glass panels 102 adjacent the inner end of the slides on which the liquid is being spread, pin 160 is urged against stationary wall 262 causing the pin 160 to be moved upwardly into the upper portion 164 of slot 162 which in turn raises arm 150 and pin 152 to raise the spreaders 100 including glass panels 102 above their respective slides. Lever 124 stops rotating when it abuts the uppermost spacer rod 14 (FIG. 7). Air from lines 306 and 308 expedites the drying of the smeared liquid on the slides. The smeared slides 42 can now be readily grasped and removed.

Figure 12:
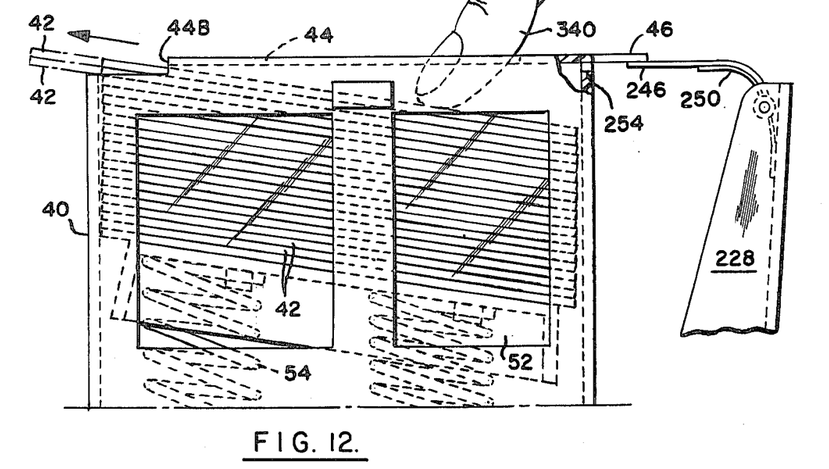
FIG. 12 is a side elevation, partially broken away, of the structure of FIG. 10 showing a pair of slides which are stuck together being removed.

In the event that the two uppermost slides 42 stick together, they cannot be moved forwardly by pusher strip 246. However, since the forward ends 44B of flange 44 are set back from the front of magazine 40, a finger indicated at 340 in FIG. 12 can lower the rear ends of the slides 42 sufficiently to permit the two uppermost slides to be moved forwardly out of the magazine together.

Referring now to FIGS. 13 through 19, a magazine 360 is generally similar to the above described magazine 40 and has an opening 362 in the top and a U-shaped flange 364 to retain slides 42. Flange 364 has notches 364A to indicate where the liquid to be smeared should be placed on the slide. A rearwardly extending tongue 366 and a slot 367 are adapted to cooperate with one of the above described pusher strips 246 in smearing device 2. Magazine 360 has a front wall 368, a rear wall 370, a right side wall 372 and a left side wall 374 and an opening 376 in the bottom thereof. A boss 380 is located on each of the side walls for cooperation with a spring clip 86 in smearing device 2. As thus described magazine 360 does not differ materially from magazine 40 described above.

Walls 368 and 370 respectively have at their lower ends protuberances 384 and 386 extending inwardly for the support of slides 42 before the magazine 360 is loaded into a smearing device 2. These protuberances are formed after the slides are loaded into the magazine 360. Advantageously magazine 360 is made of a thermoplastic synthetic resin such as, for example, polystyrene, polyamide, methyl methacrylate, polyethylene, a polyester, and polyvinylchloride resin in which case the protuberances are readily formed by subjecting walls 368 and 370 to heat and pressure to deform them. In the case of the use of a material which is deformable by pressure alone without heating, such as, for example, a metal, the protuberances 384 and 386 are formed by peening or the like after the slides 42 are inserted into magazine 360 through the bottom thereof.

Figures 13, 14, 15:
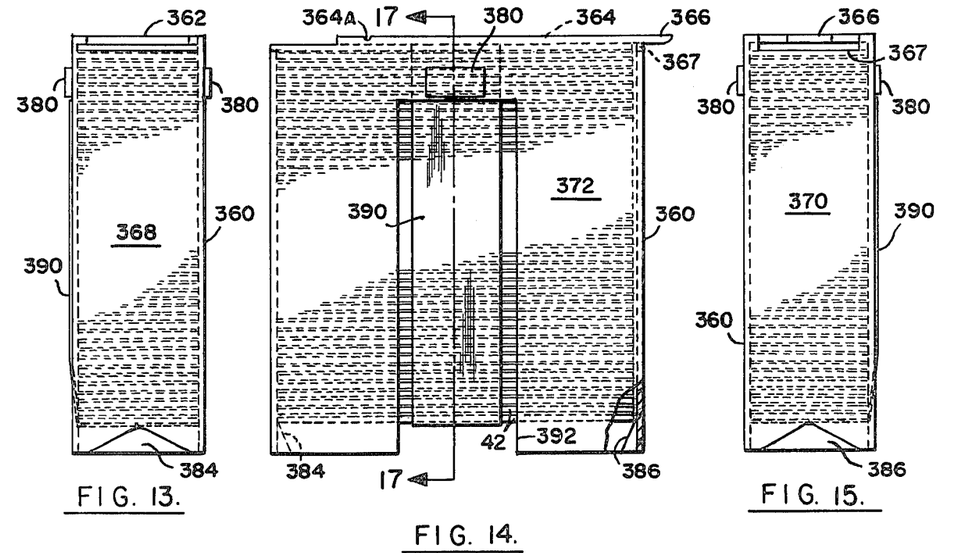
FIG. 13 is a front elevation of an alternative magazine.
FIG. 14 is a right side elevation of the magazine of FIG. 13.
FIG. 15 is a rear elevation of the magazine of FIG. 13.
Figures 16, 17:
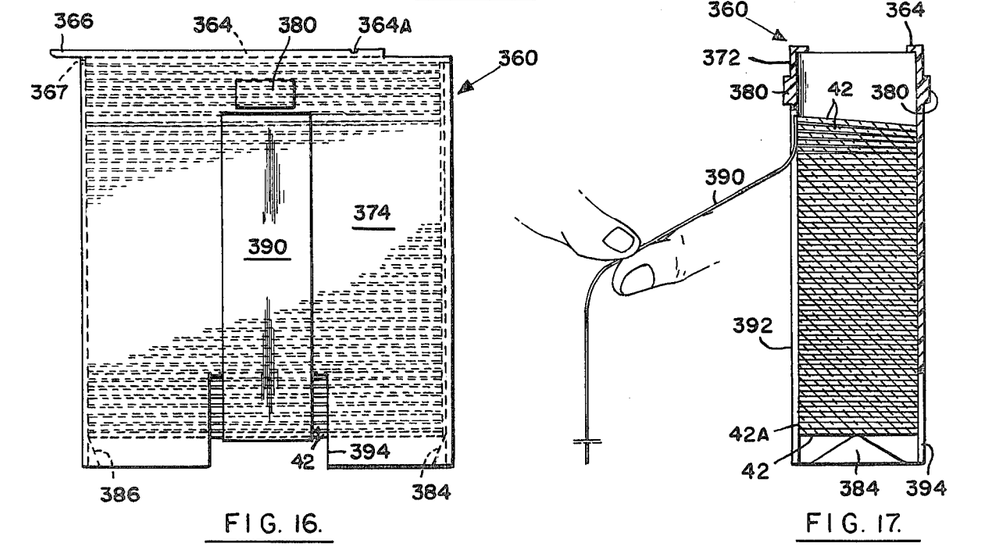
FIG. 16 is a left side elevation of the magazine of FIG. 13.
FIG. 17 is a vertical section taken on the plane indicated by the line 17—17 in FIG. 14.
Figure 18:
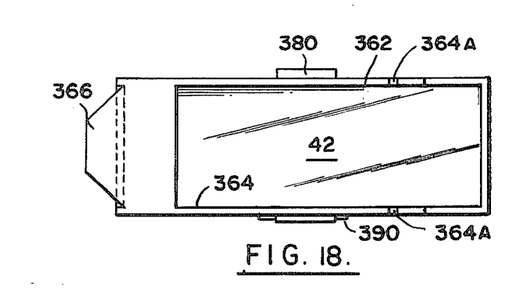
FIG. 18 is a top plan view of the magazine of FIG. 13.
Figure 19:
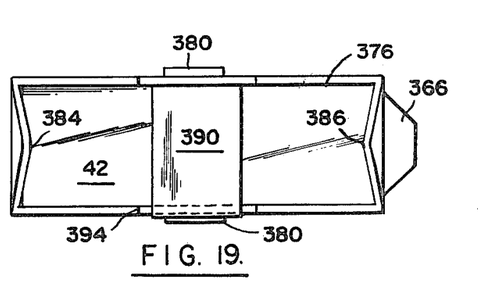
FIG. 19 is a bottom plan view of the magazine of FIG. 13.

Each of the slides 42 has an edge 42A secured to a strip of adhesive tape 390 with each slide being separated from the next adjacent slide to prevent the slides from sticking together. While each slide may be attached to the tape individually by hand, this is very time consuming and can be eliminated by employing the method disclosed in Marshall S. Levine application Serial No. 688,005 filed May 19, 1976, which is also owned by the assignee of this application, Geometric Data Corporation of Wayne, Pennsylvania. With the tape 390 secured to the side edges 42A and passing underneath the bottom slide, the slides 42 are inserted through opening 376 into magazine 360 until the uppermost slide is in contact with flange 364 and the tape passes through opening 392 in wall 372 underneath the lowermost slide 42 and thence through opening 394 in wall 374 and is then secured to wall 374 to hold the slides in position. It is at this juncture that protuberances 384 and 386 are formed to prevent the slides from passing through bottom opening 376 when the tape is removed.

Before the magazine 360 is placed in the smearing device 2, the tape 390 is stripped off slides 42 starting with the end of the tape secured to wall 374 (see FIG. 17). As tape 390 is stripped off the slides, the slides drop together causing the uppermost slide 42 to drop below the top of opening 392 permitting the tape to be removed from the uppermost slides. The magazine 360 is now ready to be placed in smearing device 2 with a clip 86 engaging boss 380 and a cap 52 urged upwardly by springs 54 and 56 passing upwardly in magazine 360 clear of protuberances 384 and 386 to urge the slides 42 upwardly.

It will be understood that the above described embodiment is illustrative and is not intended to be limiting.

We claim:

1. A device for smearing on a slide liquid placed at a predetermined point on the slide comprising:
    a slide magazine containing a plurality of slides with the uppermost slide having its upper face exposed for the reception of a drop of liquid towards one end thereof,
    a spreader adjacent the other end of the uppermost slide,
    means to advance the spreader to said predetermined point on the slide and to retract the spreader to its original position to smear a drop of liquid placed on the uppermost slide in the magazine.

2. A device in accordance with claim 1 having means to advance the uppermost slide out of the magazine and directly away from the spreader a predetermined distance to facilitate the removal of the slide by hand.

3. A device in accordance with claim 2 in which the slide advancing means advances the uppermost slide and the means to advance the spreader advances the spreader until it reaches said predetermined point on the slide in the advanced position.

4. A device in accordance with claim 3 in which the magazine has a mark to indicate said predetermined point on the uppermost slide before the slide is advanced.

5. A device in accordance with claim 1 having a pusher to advance the uppermost slide out of the magazine, an opening to the magazine for the reception of the pusher, and guide means to guide the pusher into the opening.

6. A device in accordance with claim 5 in which the opening receiving the pusher is narrower than the slides to prevent the passage of a slide through the opening.

7. A device in accordance with claim 1 having a pusher to advance the uppermost slide out of the magazine, an opening in the magazine for the reception of the pusher, including a tongue adjacent the opening to guide the pusher into the opening and resilient means to urge the pusher against the tongue to maintain the tongue at the proper level to engage the uppermost slide.

8. A device in accordance with claim 1 in which the magazine has resilient means to bias the slides upwardly and the uppermost slide is retained by opposed inwardly extending flanges spaced away from the front of the magazine to provide space for a pair of tilted slides which are stuck together to be removed simultaneously.

9. A device in accordance with claim 1 in which the spreader advancing and retracting means maintains the spreader out of contact with the slide as it advances until it approaches said predetermined point on the slide when it lowers the spreader into contact with the slide.

10. A device in accordance with claim 1 in which the spreader advancing and retracting means includes cam means to gradually reduce the speed of advance of the spreader as it approaches said predetermined point on the slide to prevent damage to the liquid.

11. A device in accordance with claim 1 in which the cam means reduces the speed all the way to zero.

12. A device in accordance with claim 1 in which the spreader advancing and retracting means maintains the spreader out of contact with the slide as it advances until it approaches said predetermined point on the slide when it lowers the spreader into contact with the slide and in which the spreader advancing and retracting means includes cam means to reduce the speed of advance of the carrier as it approaches said predetermined point on the slide to prevent damage to the liquid.

13. A device in accordance with claim 1 in which the spreader is pivotally connected to the means to advance the spreader and having means to move the pivot of the spreader to raise it to decrease the angle between the spreader and the slide as the spreader is retracted to thin the smear of liquid.

14. A device in accordance with claim 13 in which the means to move the pivot of the spreader lowers it after it is raised to increase the angle between the spreader and the slide.

15. A device for smearing on a slide a drop of liquid placed at a predetermined position on the slide comprising:
   means to support a slide with its upper face exposed for the reception of a drop of liquid at said predetermined position,
   a spreader,
   first lever means pivotally supporting the spreader and pivotally mounted at a point remote from and below the spreader,
   second pivoted lever means having an actuating portion manually moveable downwardly,
   interacting cam means on said first and second lever means to cause downward movement of the actuating portion of the second lever means to pivot the first lever means to advance the spreader until the spreader reaches said predetermined position, and
   means including a spring to return the first and second lever means to their original positions to cause the spreader to smear liquid on the slide.

16. A device in accordance with claim 15 in which the interacting cam means advance the spreader relatively rapidly to a position short of said predetermined position and then relatively slowly until the spreader reaches said predetermined position.

17. A device in accordance with claim 15 in which the pivotal mounting of the first lever means is positioned to provide for the pivot point of the spreader to be higher when the spreader is fully advanced than when the spreader is fully retracted to cause the spreader to make a greater angle with the slide in the retracted position than in the advanced position to provide a wedge shaped smear of liquid on the slide.

18. A device in accordance with claim 15 having means to elevate the spreader as it approaches its retracted position including an arm mounted on the first lever means capable of assuming a raised and a lowered position, means on said arm adapted to engage the spreader and cam means to raise and lower the arm.

19. A device in accordance with claim 15 having means to latch the first lever means with the spreader at said predetermined position on the slide and in which the means to return the levers includes a spring connected to the first lever means and a spring connected to the second lever means, interacting means on the latch and the second lever means to cause the latch to release the first lever means as the second lever means approaches its original position, and means to retard the rotation of the second lever means to its original position to provide time for the liquid to spread along the spreader.

20. A device in accordance with claim 15 in which the means to support a slide comprises a slide magazine containing a plurality of slides.

21. A device in accordance with claim 20 in which slide pusher means is connected to the second lever means to advance a slide partially out of the magazine to a position where it can be grasped by a hand.

* * * * *